(12) United States Patent
Eisert

(10) Patent No.: US 7,064,130 B2
(45) Date of Patent: Jun. 20, 2006

(54) USE OF RADICAL-SCAVENGING COMPOUNDS FOR TREATMENT AND PREVENTION OF NO-DEPENDENT MICROCIRCULATION DISORDERS

(75) Inventor: Wolfgang Eisert, Hannover (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 53 days.

(21) Appl. No.: 10/121,496

(22) Filed: Apr. 12, 2002

(65) Prior Publication Data

US 2002/0156088 A1 Oct. 24, 2002

Related U.S. Application Data

(60) Provisional application No. 60/288,605, filed on May 4, 2001.

(30) Foreign Application Priority Data

Apr. 20, 2001 (DE) .............................. 101 19 680

(51) Int. Cl.
*A61K 31/519* (2006.01)
*A61K 31/517* (2006.01)
*A61K 31/27* (2006.01)

(52) U.S. Cl. .............................. 514/259.1; 514/258.1; 514/256; 514/481

(58) Field of Classification Search ................ 514/260, 514/258, 256
See application file for complete search history.

(56) References Cited

U.S. PATENT DOCUMENTS

| 5,639,482 | A | | 6/1997 | Crary |
| 5,968,983 | A | * | 10/1999 | Kaesemeyer ................. 514/564 |
| 6,015,577 | A | * | 1/2000 | Eisert et al. ................. 424/451 |

FOREIGN PATENT DOCUMENTS

| EP | 0 457 671 A2 | 11/1991 |
| EP | 0 543 653 A1 | 5/1993 |
| EP | 1 093 814 A | 4/2001 |
| WO | WO 95 06470 A1 | 3/1995 |
| WO | WO 00 677 37 A3 | 11/2000 |

OTHER PUBLICATIONS

Dukarm et al., "Pulmonary and systemic effects of the phosphodiesterase inhibitor dipyridamole in newborn lambs with persistent pulmonary hypertension", Pediatric Research, vol. 44, pp. 831-837. (enclosed cpoy of abstract).*
Steinhorn, R.; "Control and management of pulmonary vascular tone in the newborn"; J. of Children's Memorial Hospital Chicago; 2000.
Chen, H. et al; "Fluvastatin Upregulates Inducible Nitric Oxide Synthase Expression in Cytokine-Stimulated Vascular Smooth Muscle Cells"; Hypertension 2000: 36: 923.
Simons, M.; "Molecular multitasking: statins lead to more arteries, less plaque"; Nature Medicine, vol. 6, No. 9, 2000.
Laufs, U.; "Regulation of Endothelial Nitric Oxide Synthase Production by Inhibition of HMG-CoA Reductase"; INABIS '98.
Baller, D. et al; Verbesserung der koronaren Vasodilatationskapazitaet durch medikamentoese Lipid-senkung bei Patienten im Fruehstadium der koronaren Atherosklerose mit einge schraenkter Koronarreserve und maessig-gradiger LDL-Hypercholesterinaemie; Z Kardiol 87; Suppl 2, 136-144, 1998.
Baller, D. et al; (Translation) "Improvement of Coronary Vasodilator Capacity by Lipid-lowering Therapy in Patients in the Early Stage of Coronary Atherosclerosis with Reduced Coronary Reserve and Moderate LDL-Hypercholesterolemia";Z Kardiol 87: Suppl 2, 136-144, 1998.
Marmont, et al; "Thrombotic Thrombocytopenic Purpura Successfully Treated WSith A Combination Of Dipyridamole And Aspirin"; Haematologica, 1980, 65 (2) 222-231.
Damad Study Group; "Effect of Aspirin Alone and Aspirin Plus Dipyridamole in Early Diabetic Retinopathy"; Diabetes, 1989, 38 (4), 491-498.
Connolly, et al; "Peripheral Vasodilators and the Management of Peripheral Vascular Disease and Raynaud's Syndrome in General Practice"; Pharmacoepidemiology and Drug Safety, 1998, 7, 189-196.
Kaiser, et al; "Short-term effect of dipyridamole on blood flow velocities in the extraocular vessels"; International Ophthalmology, 19, 6, 1996, 355-358.

(Continued)

*Primary Examiner*—Kevin E. Weddington
(74) *Attorney, Agent, or Firm*—Paula K. Wittmayer; Michael P. Morris; Mary-Ellen M. Devlin

(57) ABSTRACT

A method of treatment of the human or non-human animal body for treating NO-dependent microcirculation disorders is disclosed, for example microcirculation disorders caused by metabolic diseases, such as elevated levels of homocystin-homocystein inflammatory reactions or autoimmune diseases, furthermore peripheral microcirculation disorders or microcirculation disorders associated with increased cell fragmentation, which method comprises administering to a human or non-human animal body in need of such treatment an effective amount of a pharmaceutical composition containing a substance which scavenges free radicals, e.g. a pyrimido-pyrimidine selected from Dipyridamole, Mopidamol and the pharmaceutically acceptable salts thereof, and the use such substance for the manufacture of a corresponding pharmaceutical composition, optionally in combination with an agent capable of increasing NO procution.

8 Claims, No Drawings

OTHER PUBLICATIONS

Abstract: Derwent Pub. & SU 1 711 894 A (Kiev Child Clinic-2), Feb. 15, 1992.

Abstract: Derwent Pub. & SU 1 711 892 A (Mosc. Heamatology Blood Transfusion Inst.); Feb. 15, 1992.

Abstract: Denton, et al; "Probucol improves symptoms and reduces lipoprotein oxidation susceptibility in patients with Raynaud's phenomenon" & Rheumatology (Oxford, England) England, 1999, vol. 38, No. 4.

Abstract: Sharma et al; "Probucol suppresses oxidant stress in hypertensive arteries. Immunohistochemical evidence." & Am. J of Hypetension: J Am Soc of Hypertension. US, 1996, vol. 9, No. 6, 1996, 577-590.

Abstract: ADEE; "Managing Reynaud's phenomenon: a practical approach."; & Am Family Phys. US; 1993, vol. 47, No. 4, 823-829.

Abstract: Ballmer, et al; "Antioxidant vitamins and disease—risk of a suboptimal supply!" & Therapeutische Umschau. Revue Therapeutique. Switzerland, 1994, vol. 51, No. 7, 467-474.

Abstract: Ali, et al; "Role of plasma ascorbate in diabetic microangiopathy." & Bangladesh Medical Research Council Bulletin, Bangladesh, 1989, vol. 15, No. 2, 47-59.

Abstract: Yoshida, et al; "Effect of alpha-tocopherol, taurine and selenium on the attenuation of ischemia/reperfusion injury of splanchnic organs."; & Cardiovascular Surgery (London, England) England, 1998, vol. 6, No. 2, 178-187.

Abstract: Kempski, et al; "Neuroprotection. Models and basic principles!"; & Der Anaesthesist. Germany, 1994, S25-S33.

Abstract: Langleben, et al; "Effects of dimethylthiourea on chronic hypoxia induced pulmonary arterial remodelling and ventricular hypertrophy in rats."; & Clinical and Investigative Medicine. Medecine Clinique et Experimentale., Canada, 1989. vol. 12. No. 4. 235-240.

Abstract: Bertuglia, et al; "Glucose-insulin-potassium treatment in combination with dipyridamole inhibits ischaemia-reperfusion-induced damage." & Diabetologia. Germany, 2001, vol. 44, No. 12, 2165-2170.

* cited by examiner

USE OF RADICAL-SCAVENGING COMPOUNDS FOR TREATMENT AND PREVENTION OF NO-DEPENDENT MICROCIRCULATION DISORDERS

RELATED APPLICATIONS

Benefit of U.S. Provisional Application Ser. No. 60/288,605, filed on May 4, 2001, is hereby claimed.

FIELD OF THE INVENTION

This invention relates to a method of treatment of disorders of the microcirculation, particularly those where insufficient generation of NO seems to be the cause of the problem, using substances to scavange free radicals such as Dipyridamole or Mopidamol in doses lower than those needed to directly inhibit platelet aggregation alone or in combination with substance to increase cellular Nitric oxide (NO) production such as HMG CoA reductase inhibitors at doses below the typical dose to lower serum lipids but sufficient to still enhance eNOS in cells of the vasculature.

BACKGROUND OF THE INVENTION

By laboratory models reflecting the complex physiology of the blood vessel it could be shown that the vasculature is not a passive conduit, but interacts profoundly with the blood through an intricate system of checks and balances to protect its integrity after vascular accident. Therefore the endothelium produces prostacyclin, a potent inhibitor of aggregation. The normal endothelium is not thrombogenic and prevents the attachment of platelets. Various stimulants precipitate the release of endothelium-derived relaxing factor (EDRF), which inhibits platelet adhesion and aggregation. At the same time, intracellular increase in cGMP was shown to be responsible for relaxation of smooth muscle cells following administration of nitro compounds. Thus the endothelium can provide maintenance of local perfusion of the vessels by several separate mechanisms, one being the local vasodilatation mediated by prostacyclin and Nitric Oxide (NO, also described in literature as EDRF) and another being the decreased interaction of blood cells with each other or the negative interaction of white blood cells or blood platelets with the cells of the vessel wall. Another would be the control of local fibrin accumulation by controlling the formation as well as lysis of already formed strands of fibrin. In larger vessels aggregation and adhesion of platelets to damaged parts of the vessel wall particularly after interventional therapy play an important role and have been shown to be treated with inhibitors of platelet aggregation (see WO 98/11896). The benefit of enhancing endothelial NO synthesis by HMG CoA reductase inhibitors has been described in U.S. Pat. No. 5,968,983 and WO 00/56403.

In the past prevention and treatment of conditions causing reduced tissue perfusion have been focussed mainly on mechanical as well as pharmaceutical re-vasularisation of the larger arteries supplying blood to a larger area of tissue. The focus did lay on either preventing build-up of atherosclerotic plaques (lipid lowering therapy) or on the prevention of the thromboembolic occlusion triggered by rupturing plaque and activation of platelet aggregation leading often to an occlusive thrombus. This is the reason why major efforts have been focussed on inhibition of aggregation of platelets, ultimately by blocking the final common pathway of platelet aggregation, i.e. by inhibiting the receptor for fibrinogen on platelets, the final step of linking platelets together when forming a platelet rich thrombus. It therefore is also straight forward to combine lipid lowering therapy with potent platelet aggregation inhibitors of combinations of such as tought in WO 98/11896.

In addition, procedures for fast and safe revascularisation of the occluded arteries have been developed such as pharmacological lysis of thrombi with thrombolytic agents such as r-tPA or mechanically by transcutaneous intravascular balloon angioplasty. Again here the major problem remaining is the acute rethrombosis of the reopened segment of the blood vessel, where strong inhibitors of platelet aggregation or the combination of platelet inhibition with inhibitors of fibrin formation have shown to be effective.

In preventing reoccurence of myocardial infarcts (MI), chronic application of mild platelet inhibitors such as Aspirin have shown only limited efficacy (published meta analysis aggree to a reduction of the incidence by 18%). Using more potent platelet inhibitors such as various orally available inhibitors of the platelet fibrinogen receptor however have shown no improvement over the effect achieved by ASA. More than 37,000 patients have been subjects in major studies on the long term benefit of chronic administration of oral fibrinogen receptor antagonists in preventing cardiovascular events. All studies have been negative, in fact the treatment arm showed a higher risk for bleeding and increased mortality.

This concludes that long term benefit can not be extrapolated from the clear short term benefit of very strong inhibition of platelet aggregation even when combined with therapy designed to reduce the build up of atherosclerotic plaques or the elevated risk related to elevated levels of plasma lipids as done by lipid lowering therapy.

DESCRIPTION OF THE INVENTION

Tissue perfusion is vital to the health and survival and function of any organ, particularly those organs with high oxygen and nutritive demand. Even after successful revascularisation of epicardial arteries the perfusion of the tissue, i.e. the properties of the microcirculation have been shown to significantly influence the mortality after MI at 90 days (Gibbson at all, Circulation 2000, 101:125–130), resulting in a reduction of mortality from 4.6% to 0.8%, in cases where tissue perfusion, was not reduced, i.e. microcirculation was not compromised.

This present invention focuses on the importance of tissue perfusion on the level of smaller vessels downstream of the large vessels, supplying tissue with oxygen and nutrients by improving microcirculation. Microcirculation disorders, i.e. circulation disorders caused by microvascular dysfunction, can be caused by metabolic or oxidative stress leading to diseases where vascular dysfunction or damages are involved.

The present invention provides a new approach for improving microcirculation by treatment and/or prevention of such disorders of microcirculation which are caused by reduced endogenous NO production by cells otherwise needed for local prevention of vessel spasm or loss of dilatory reactivity as well as prevention of cell mediated damage. The improvement of NO-dependent microvascular dysfunction is especially important in small vessels or capillary vessels where the ratio of vessel wall surface area to blood volume is high, and provides a new approach for treatment and prevention of disorders of the NO. Therefore, radical scavengers like Dipyridamole and Mopidamol alone or in combination with substance capable of increasing NO production may have therapeutic potential in a variety of diseases involving progressive dysfunction of medium and small-sized vessels.

Accordingly, disorders of the microcirculation according to the present invention are meant to be those where by metabolic or genetic influence the cells of the vasculature are no longer able to produce sufficient amount of NO, the potent local regulator of homeostasis in the vascular system. Such disorders are named herein "NO-dependent microcirculation disorders". Examples of such disorders are diabetic angiopathy, especially diabetic microangiopathy, e.g. diabetic gangrene, diabetic retinopathy, diabetic neuropathy, or such as hyperhomocysteinemia, homocysteinuria, pulmonary hypertension, mucoviscidosis, neuro-degenerative disease, ulcus cruris, atrophic gastritis, colitis ulcerosa, or microcirculation disorders occuring after partial resection of stomach and/or bowels;

furthermore re-establishment of blood flow upon insufficient tissue perfusion after revascularisation of large arteries such as after acute MI or Stroke or in peripheral artery disease in addition or following acute antiplatelet therapy to prevent acute reocclusion, e.g. as disclosed in WO 98/11896;

similarly conditions where dysfunction is caused by re-perfusion injury after revascularisation or in transplant recipient;

microcirculation disorders caused by inflammatory reactions, such as morbus crohn, colitis ulcerosa or acute respiratory dystress syndrome (ARDS);

microcirculation disorders caused by autoimmune diseases, such as autoimmune chronic-active hepatitis (idiopathic hepatitis), primary-biliary cirrhosis or (autoimmune associated) multiple sclerosis;

peripheral microcirculation disorders, such as Raynaud's disease, tinnitus or sudden loss of hearing;

microcirculation disorders associated with increased cell fragmentation, such as tumor diseases or thrombotic-thrombocytopenic purpura (TTP); and nephrosclerosis, prerenal hypertension, haemolytic-uremic syndrome (HUS), arterial hypertension, vascular dementia, Alzheimer's disease, Sudeck's disease, central-veneous thrombosis of the eye, ischemic optic neuropathy, homocystine-induced vasculopathy, ischemic or coronary heart diseases, prevention of myocardial infarction or reinfarction, treatment or prevention of atherosclerosis, degenerative diseases ofjoints such as arthritis.

The indication "NO-dependent microcirculation disorders" further includes corresponding disorders of the myocardium. Thus the present invention provides a method for improving the blood supply of the myocardium in a person in need of such treatment, for example in a person suffering from ischemic or coronary heart disease, as well as a method for prevention of myocardial infarction or re-infarction. This in particular after successful reperfusion by mechanical or pharmacological revascularisation and in parallel or after the inhibition of acute rethrombosis/reocclusion by strong inhibitors of platelet aggregation.

Furthermore, treatment of "NO-dependent microcirculation disorders" within the present invention also includes treatment or prevention of atherosclerosis by improving perfusion through the vasa vasorum of large vessels.

NO-dependent disorders of the microcirculation can be approached by either increasing the local production of NO or, preferably, by combining the increase of NO with reducing the local destruction of NO.

Preferred is pulmonary hypertension; re-establishment of blood flow upon insufficient tissue perfusion after revascularisation of large arteries such as after acute MI or Stroke or in peripheral artery disease in addition or following acute antiplatelet therapy to prevent acute reocclusion, e.g. as disclosed in WO 98/11896; conditions where dysfunction is caused by re-perfusion injury after revasularisation or in transplant recipient; peripheral microcirculation disorders, such as Raynaud's disease, tinnitus or sudden loss of hearing;

vascular dementia, Alzheimer's disease; homocysteinuria and homocystine-induced vasculopathy;

ischemic or coronary heart diseases; prevention of myocardial infarction or reinfarction; and treatment or prevention of atherosclerosis.

Most preferred indication to be treated according to the present invention is insufficient tissue perfusion after revascularisation of large arteries such as after acute MI or Stroke or re-establishment of blood flow in peripheral artery disease in addition or following acute antiplatelet therapy to prevent acute reocclusion; homocysteinuria and homocystine-induced vasculopathy; and vascular dementia.

It is found that a substance which scavenges free radicals increases the local production of NO. Accordingly, NO-dependent microcirculation disorders can be treated according to the present invention by a method of treatment comprising a substance which scavenges free radicals.

Preferred is a substance that scavenges free oxy- and/or peroxi-radicals.

Further preferred is a substance that is membrane bound and scavenges oxy- and peroxy radicals.

Compounds acting as scavengers according to the present invention are, for example, Probucol, Ascorbic acid, Alpha tocopherol, Dipyridamole or Mopidamol;

preferred is

Dipyridamole and Mopidamol;

most preferred is Dipyridamole.

A said substance is applied optionally in combination with an agent capable of increasing NO production. A compound capable to increase NO production according to the present invention is, for example, Acetylcholine estrogen, or HMG CoA reductase inhibitors such as Lovastatin, Pravastatin, Simvastatin, Fluvastatin, Dalvastatin, Compactin, Mevastatin, HR 780, BMY 22,089, BMY 22,566, SQ 33,600, GR 95,030 or CI 981;

preferred is Lovastatin, Pravastatin, Simvastatin, Fluvastatin, Dalvastatin, Compactin, Mevastatin, HR 780, BMY 22,089, BMY 22,566, SQ 33,600, GR 95,030 or CI 981;

more preferred is Lovastatin, Pravastatin, Simvastatin, Fluvastatin, Dalvastatin, Compactin, Mevastatin.

Preferred is the combination of Mopidamol or even more preferred Dipyridamole with an agent selected from the class of HMG CoA reductase inhibitors. The combination of sub-/or therapeutical doses of HMG CoA reductase inhibitors known to upregulate expression of eNOS (endothelial nitric oxide synthetase), which have clinical benefit at lipid lowering doses, with doses of Dipyridamole or Mopidamol, which inhibits destruction of NO.

If the substance which scavenges free radicals is chosen as Dipyridamole or Mopidamol it is of advantage to maintain a plasma level of Dipyridamole or Mopidamol of about 0.2 to 5 µmol/L, preferably of about 0.4 to 5 µmol/L, especially of about 0.5 to 2 µmol/L or particularly of about 0.8 to 1.5 µmol/L or when combined with HMO CoA reductase inhibitors at 0.2 to 2.0 µmol/L. This can be achieved using any of the oral Dipyridamole retard, instant or the parenteral formulations on the market, the retard formulations being preferred, for instance those available under the trademark Persantin®, or, for an optional additional combination therapy with low-dose acetyl salicylic acid (ASA), using those formulations available under the trademark Asasantin ® or Aggrenox®. Dipyridamole retard formulations are also disclosed in EP-A-0032562, instant formulations are disclosed in EP-A-0068191 and combinations of ASA with Dipyridamole are disclosed in EP-A-0257344 which are incorporated by reference. In case of Mopidamol also oral retard, instant or a parenteral formulations can be used, e.g. those disclosed in GB 1,051,218 or EP-A-0,108,898 which are incorporated by reference, retard formulations being preferred.

Dipyridamole or Mopidamol can be administered orally in a daily dosage of 25 to 450 mg, preferably 50 to 240 mg, most preferred 75 to 200 mg. For long-term treatment it is of advantage to administer repeated doses such as a dose of 25 mg Dipyridamole retard or any other instant release formulation three or four times a day. For parenteral administration Dipyridamole could be given in a dosage of 0.5 to 5 mg/kg body weight, preferably 1 to 3.5 mg/kg body weight, during 24 hours as slow i.v. infusion (not faster than 0.2 mg/min).

Dipyridamole {2,6-bis(diethanolamino)-4,8-dipiperidino-pyrimido[5,4-d]pyrimidine}, closely related substituted pyrimido-pyrimidines and their preparation have been described in e.g. U.S. Pat. No. 3,031,450. Further related substituted pyrimido-pyrimidines and their preparation have been described in e.g. GB 1,051,218, inter alia the compound Mopidamol {2,6-bis(diethanolamino)-4-piperidinopyrimido[5,4-d]pyrimidine}. Dipyridamole was introduced as a coronary vasodilator in the early 1960s. It is also well known having platelet aggregation inhibitor properties due to the inhibition of adenosine uptake. However, at doses above the dose range and therapeutically in the Aggrenox® preparation. Whereas the activity of Dipyridamole and Mopidamol as platelet aggregation inhibitor directly in high concentrations and indirectly through the inhibition of Adenosine reuptake at therapeutic plasma levels is well known it is a new finding that these agents additionally are inhibitors of NO destruction mediated by their capacity to scavange oxi- as well as peroxi radicals while being bound to membranes of cells of the vessel wall.

Previous investigations led to its use as an antithrombotic agent; it soon became the therapy of choice for such applications as stroke prevention, maintaining the patency of coronary bypass and valve-replacement, as well as for treatment prior to coronary angioplasty.

Furthermore, the European Stroke Prevention Study 2 (ESPS-2; J Neurol Sci. 1996; 143: 1–13; Neurology 1998; 51: 17–19) proved that treatment by Dipyridamole alone was as effective as low-dose aspirin in the reduction of stroke risk, and combination therapy with Dipyridamole and aspirin was more than twice as effective as aspirin alone.

Dipyridamole appears to inhibit thrombosis through multiple mechanisms. Early studies showed that it inhibits the uptake of adenosine, which was found to be a potent endogenous anti-thrombotic compound. Dipyridamole was also shown to inhibit cyclic AMP ph6sphodiesterase, thereby increasing intracellular c-AMP.

Dipyridamole appears to enhance of above-mentioned antithrombotic mechanisms (cAMP—increase, cGMP—increase) of the vessel wall, in addition to its adenosine-sparing effects. It stimulates prostacyclin production by increasing intracellular levels of cAMP, and it enhances the strongly nitric oxide system by increasing cGMP. It further prevents local fibrin formation.

Dipyridamole also has antioxidant properties (Free Radic. Biol. Med. 1995; 18:239–247) that may contribute to its antiatherosclerotic effect. When oxidized, low density lipoproteins become recognized by the scavenger receptor on macrophages, which is assumed to be the necessary step in the development of atherosclerosis (Ann. Rev. Med. 1992; 43: 219–25).

Dipyridamole has been found to inhibit fibrinogenesis in experimental liver fibrosis (Hepatology 1996; 24: 855–864) and to suppress oxygen radicals and proteinuria in experimental animals with aminonucleoside nephropathy (Eur. J. Clin. Invest. 1998; 28: 877–883; Renal Physiol. 1984; 7: 218–226). Inhibition of lipid peroxidation also has been observed in human nonneoplastic lung tissue (Gen. Pharmacol. 1996; 27: 855–859).

Viewed from one aspect the present invention provides a method of treatment of the human or non-human animal body, preferably mammalian body, for treating or preventing NO-dependent microcirculation disorders or of disease states where such microcirculation disorders are involved, said method comprising administering to said body an effective amount of a pharmaceutical composition comprising a substance with scavenges fre radicals, according to the invention, optionally in combination with one or more agents capable of increasing NO production.

A preferred aspect the present invention provides the use of a pyrimido-pyrimidine selected from Dipyridamole, Mopidamol and the pharmaceutically acceptable salts thereof, Dipyridamole being preferred, optionally in combination with one or more agents capable of increasing NO production, preferably selected form the class of HMG Co-Areductase inhibitors, for the manufacture of a pharmaceutical composition for the treatment of the human or non-human animal body, preferably mammalian body, for treating or preventing NO-dependent microcirculation disorders or of disease states where such microcirculation disorders are involved.

EXAMPLES

Experimentally this condition is tested in animal models showing deficiency of microcirculatory function. Animal models used are experimental stroke models in rats and mice as well as in non-rodent animals including non-human primates.

In the stroke models the size of tissue damage after occlusion of an artery feeding a well defined area of the brain tissue is evaluated by histology and non-invasive imaging, measuring the extent of regional perfusion and tissue damage (MRI, CT).

The size of the infarcted tissue is found to be dependent on the capacity of the microcirculatory system to provide blood flow in the periphery under conditions of oxidative and metabolic stress. The size of the infarcted tissue is smaller after treatment with a combination of Dipyridamole and pravastatin. The same effect can be shown with other agents selected from the class of HMG CoA reductase inhibitors.

Further experiments are carried out with another animal model: genetically engineered NO Synthetase knock-out mice are used where NO synthetase activity is blocked or partially inhibited, respectively. By employing experimental conditions in such a model under which the NO Synthetase activity is blocked or reduced the effect of Dipyridamole in preventing NO destruction is investigated and compared with the influence of pravastatin on elevating NO production. Thereby the effect of NO sparing is seen as independent effect in cases were increase of NO production is limited.

The testing in animal models and subsequently in clinical trials with volunteers and patients includes testing of the efficacious dose range according to good clinical practice.

What is claimed is:

1. A method of treating an animal for NO-dependent microcirculation disorders selected from the group consisting of
hyperhomocysteinemia, homocysteinuria, mucoviscidosis, atrophic gastritis, colitis ulcerosa, partial resection of stomach and/or bowels, and acute respiratory distress syndrome (ARDS), which comprises administering to the animal an effective amount of a pharmaceutical composition comprising dipyridamole, or a pharmaceutically acceptable salts thereof.

2. The method according to claim 1 wherein dipyridamole is administered in combination with one or more HMG CoA reductase inhibitors which are capable of increasing NO production.

3. The method of claim 1, characterized in that a plasma level of about 0.2 to 5 µmol/L dipyridamole is maintained.

4. The method of claim 1, characterized in that dipyridamole is administered orally in a sustained or controlled release formulation.

5. The method of claim 1, characterized in that dipyridamole is administered orally in a daily dosage of 25 to 450 mg or parenterally in a dosage of 0.5 to 5 mg/kg body weight over 24 hours.

6. The method of claim 2, wherein the HMG CoA reductase inhibitor is selected from the group consisting of:
lovastatin,
pravastatin,
simvastatin,
fluvastatin,
dalvastatin,
compactin, mevastatin,
HR 780,
BMY 22,089,
BMY 22,566,
SQ 33,600,
GR 95,030 and
CI 981.

7. The method of claim 2, wherein the HMG CoA reductase inhibitor is selected from the group consisting of:
lovastatin,
pravastatin,
simvastatin,
fluvastatin,
dalvastatin, and mevastatin.

8. The method of claim 2, wherein the HMG CoA reductase inhibitor is pravastatin.

* * * * *